(12) United States Patent
Schorzman et al.

(10) Patent No.: US 7,781,558 B2
(45) Date of Patent: Aug. 24, 2010

(54) HYDROPHILIC SILOXANYL MONOMERS WITH PENDANT POLYMERIZABLE GROUPS

(75) Inventors: Derek A. Schorzman, Cary, NC (US); Joseph C. Salamone, Boca Raton, FL (US); Jay F. Kunzler, Canadaigua, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 558 days.

(21) Appl. No.: 11/830,885

(22) Filed: Jul. 31, 2007

(65) Prior Publication Data

US 2008/0076893 A1    Mar. 27, 2008

Related U.S. Application Data

(60) Provisional application No. 60/847,546, filed on Sep. 27, 2006.

(51) Int. Cl.
C08G 77/28 (2006.01)
C08G 77/30 (2006.01)

(52) U.S. Cl. ......................................... 528/30; 526/279

(58) Field of Classification Search ................... 528/30; 526/279

See application file for complete search history.

(56) References Cited

U.S. PATENT DOCUMENTS

| | | | |
|---|---|---|---|
| 3,808,179 A | 4/1974 | Gaylord | |
| 4,153,641 A | 5/1979 | Deichert et al. | |
| 4,686,267 A | 8/1987 | Ellis et al. | |
| 4,910,277 A | 3/1990 | Bambury et al. | |
| 4,977,229 A * | 12/1990 | Culberson et al. | 528/26 |
| 5,034,461 A | 7/1991 | Lai et al. | |
| 5,070,215 A | 12/1991 | Bambury et al. | |
| 5,321,108 A | 6/1994 | Kunzler et al. | |
| 5,358,995 A | 10/1994 | Lai et al. | |
| 5,374,662 A | 12/1994 | Lai et al. | |
| 5,387,662 A | 2/1995 | Kunzler et al. | |
| 5,420,324 A | 5/1995 | Lai et al. | |
| 5,451,651 A | 9/1995 | Lai | |
| 5,496,871 A | 3/1996 | Lai et al. | |
| 5,539,016 A | 7/1996 | Kunzler et al. | |
| 5,594,085 A | 1/1997 | Lai | |
| 5,610,252 A | 3/1997 | Bambury et al. | |
| 5,639,908 A | 6/1997 | Lai | |
| 5,648,515 A | 7/1997 | Lai | |
| 7,468,397 B2 | 12/2008 | Schorzman | |
| 7,528,208 B2 | 5/2009 | Schorzman et al. | |
| 7,557,231 B2 | 7/2009 | Schorzman et al. | |
| 7,601,766 B2 | 10/2009 | Schorzman et al. | |
| 7,622,512 B2 | 11/2009 | Schorzman et al. | |

OTHER PUBLICATIONS

U.S. Appl. No. 11/341,209, filed Jan. 27, 2006, Schorzman et al.
U.S. Appl. No. 11/403,393, filed Apr. 13, 2006, Schorzman et al.
U.S. Appl. No. 11/480,111, filed Jun. 30, 2006, Schorzman et al.
U.S. Appl. No. 11/480,170, filed Jun. 30, 2006, Schorzman et al.
U.S. Appl. No. 11/611,508, filed Dec. 15, 2006, Schorzman et al.
U.S. Appl. No. 11/611,512, filed Dec. 15, 2006, Schorzman et al.
U.S. Appl. No. 11/619,211, filed Jan. 3, 2007, Schorzman et al.
U.S. Appl. No. 11/837,049, filed Aug. 10, 2007, Kunzler et al.
U.S. Appl. No. 11/840,650, filed Aug. 17, 2007, Salamone et al.
U.S. Appl. No. 12/018,910, filed Jun. 24, 2008, Stanbro et al.
U.S. Appl. No. 12/313,253, filed Nov. 18, 2008, Schorzman.
U.S. Appl. No. 12/459,778, filed Jul. 8, 2009, Kunzler et al.
U.S. Appl. No. 12/459,779, filed Jul. 8, 2009, Kunzler et al.
William J. Benjamin, et al., "The Oxygen Permeability of Reference Materials," Optom Vis Sci 7 (12s); 95 (1997).

* cited by examiner

*Primary Examiner*—Kuo-Liang Peng
(74) *Attorney, Agent, or Firm*—Glenn D. Smith; M. Carmen & Associates, PLLC

(57) ABSTRACT

The present invention relates to polymeric compositions useful in the manufacture of biocompatible medical devices. More particularly, the present invention relates to certain hydrophilic monomers capable of polymerization to form polymeric compositions having desirable physical characteristics useful in the manufacture of ophthalmic devices. The polymeric compositions comprise polymerized hydrophilic siloxanyl monomers.

14 Claims, No Drawings

HYDROPHILIC SILOXANYL MONOMERS WITH PENDANT POLYMERIZABLE GROUPS

PRIORITY CLAIMS TO PRIOR APPLICATIONS

This application claims the benefit of Provisional Patent Application No. 60/847,546 filed Sep. 27, 2006 and is incorporated herein by reference.

FIELD

The present invention relates to polymeric compositions useful in the manufacture of biocompatible medical devices. More particularly, the present invention relates to certain hydrophilic siloxanyl monomers capable of polymerization to form polymeric compositions having desirable physical characteristics useful in the manufacture of ophthalmic devices.

BACKGROUND AND SUMMARY

Various articles, including biomedical devices, are formed of organosilicon-containing materials. One class of organosilicon materials useful for biomedical devices, such as soft contact lenses, is siloxy-containing hydrogel materials. A hydrogel is a hydrated, crosslinked polymeric system that contains water in an equilibrium state. Hydrogel contact lenses offer relatively high oxygen permeability as well as desirable biocompatibility and comfort. The inclusion of a siloxy-containing material in the hydrogel formulation generally provides higher oxygen permeability since siloxy-based materials have higher oxygen permeability than water.

Another class of organosilicon materials is rigid, gas permeable materials used for hard contact lenses. Such materials are generally formed of silicon or fluorosilicon copolymers. These materials are oxygen permeable, and more rigid than the materials used for soft contact lenses. Organosilicon-containing materials useful for biomedical devices, including contact lenses, are disclosed in the following U.S. patents: U.S. Pat. No. 4,686,267 (Ellis et al.); U.S. Pat. No. 5,034,461 (Lai et al.); and U.S. Pat. No. 5,070,215 (Bambury et al.).

Siloxy-containing materials are of keen interest as ophthalmic materials as they have characteristically high gas permeability, but suffer the disadvantage of being very hydrophobic. This hydrophobicity results in poor wettability and comfort of the resulting materials when in contact with the cornea, and creates difficulty in compatibilizing such siloxy-containing monomers with hydrophilic monomers to result in a transparent copolymer with an ideal blend of properties.

Soft contact lens materials are made by polymerizing and crosslinking hydrophilic monomers such as 2-hydroxyethyl methyacrylate, N-vinyl-2-pyrrolidone, methacrylic acid and combinations thereof. The polymers produced by polymerizing these hydrophilic monomers exhibit significant hydrophilic character themselves and are capable of absorbing a significant amount of water in their polymeric matrices. Due to their ability to absorb water, these polymers are often referred to as "hydrogels." These hydrogels are optically clear and, due to their high levels of water of hydration, are particularly useful materials for making soft contact lenses. Siloxane-type monomers are well known to be poorly soluble in water as well as hydrophilic solvents and monomers and are therefore difficult to copolymerize and process using standard hydrogel techniques.

The present invention provides novel hydrophilic organosilicon-containing monomers which are useful in articles such as biomedical devices including contact lenses.

BRIEF DESCRIPTION OF THE DRAWINGS

None

DETAILED DESCRIPTION

In a first aspect, the invention relates to monomers of Formula (I):

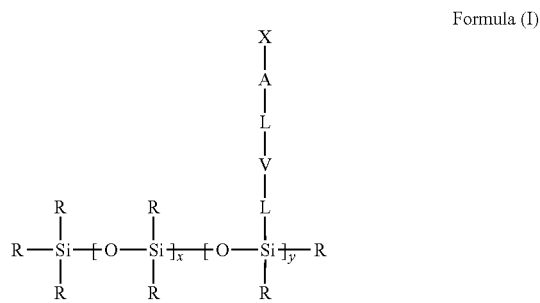

Formula (I)

wherein L, when present, can be the same or different and is selected from the group consisting of a bond, a straight or branched C1-C30 alkyl group, a C1-C30 fluoroalkyl group, a C1-C20 ester-containing group, an alkyl ether, cycloalkyl ether, cycloalkenyl ether, aryl ether, arylalkyl ether, a polyether-containing group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, a C5-C30 fluoroaryl group, or a hydroxyl substituted alkyl ether and combinations thereof; A is a residue capable of forming organic acids, salts or esters selected from the group consisting of sulfonates, sulfates, sulfites, phosphates, phosphites, pyrophosphates and phosphonates; X is H, one equivalent alkali metal, or ½ equivalent alkaline earth metal; R is independently hydrogen, a straight or branched C1-C30 alkyl group, a C1-C30 fluoroalkyl group, a C1-C20 ester-containing group, an alkyl ether, cycloalkyl ether, cycloalkenyl ether, aryl ether, arylalkyl ether, a polyether-containing group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, fluorine, a C5-C30 fluoroaryl group, or a hydroxyl group; and V is independently a polymerizable ethylenically unsaturated organic radical. It should be realized that the polymerizable ethylenically unsaturated organic radical may be internal or external to the L groups as shown in the figures below.

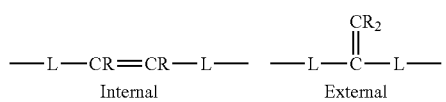

Sulfonates are salts or esters of sulfonic acid, while sulfites are salts or esters of sulfinic acid and sulfates are salts or esters of sulfuric acid. Phosphates are salts or esters of phosphoric acid, while phosphates are salts or esters of phosphinic acid. Pyrophosphates are salts or esters of pyrophosphoric acid. Phosphonates are salts or esters of phosphonic acid.

Representative examples of urethanes for use herein include, by way of example, a secondary amine linked to a carboxyl group which may also be linked to a further group such as an alkyl. Likewise the secondary amine may also be linked to a further group such as an alkyl.

Representative examples of carbonates for use herein include, by way of example, alkyl carbonates, aryl carbonates, and the like.

Representative examples of carbamates, for use herein include, by way of example, alkyl carbamates, aryl carbamates, and the like.

Representative examples of carboxyl ureidos, for use herein include, by way of example, alkyl carboxyl ureidos, aryl carboxyl ureidos, and the like.

Representative examples of sulfonyls for use herein include, by way of example, alkyl sulfonyls, aryl sulfonyls, and the like.

Representative examples of alkyl groups for use herein include, by way of example, a straight or branched hydrocarbon chain radical containing carbon and hydrogen atoms of from 1 to about 18 carbon atoms with or without unsaturation, to the rest of the molecule, e.g., methyl, ethyl, n-propyl, 1-methylethyl (isopropyl), n-butyl, n-pentyl, etc., and the like.

Representative examples of fluoroalkyl groups for use herein include, by way of example, a straight or branched alkyl group as defined above having one or more fluorine atoms attached to the carbon atom, e.g., —CF3, —CF2CF3, —CH2CF3, —CH2CF2H, —CF2H and the like.

Representative examples of ester-containing groups for use herein include, by way of example, a carboxylic acid ester having one to 20 carbon atoms and the like.

Representative examples of ether or polyether-containing groups for use herein include, by way of example, an alkyl ether, cycloalkyl ether, cycloalkylalkyl ether, cycloalkenyl ether, aryl ether, arylalkyl ether wherein the alkyl, cycloalkyl, cycloalkylalkyl, cycloalkenyl, aryl, and arylalkyl groups are defined above, e.g., alkylene oxides, poly(alkylene oxide)s such as ethylene oxide, propylene oxide, butylene oxide, poly(ethylene oxide)s, poly(ethylene glycol)s, poly(propylene oxide)s, poly(butylene oxide)s and mixtures or copolymers thereof, an ether or polyether group of the general formula —R8OR9, wherein R8 is a bond, an alkyl, cycloalkyl or aryl group as defined above and R9 is an alkyl, cycloalkyl or aryl group as defined above, e.g., —CH2CH2OC6H5 and —CH2CH2OC2H5, and the like.

Representative examples of amide groups for use herein include, by way of example, an amide of the general formula —R10C(O)NR11R12 wherein R10, R11 and R12 are independently C1-C30 hydrocarbons, e.g., R10 can be alkylene groups, arylene groups, cycloalkylene groups and R11 and R12 can be alkyl groups, aryl groups, and cycloalkyl groups as defined herein and the like.

Representative examples of amine groups for use herein include, by way of example, an amine of the general formula —R13NR14R15 wherein R13 is a C2-C30 alkylene, arylene, or cycloalkylene and R14 and R15 are independently C1-C30 hydrocarbons such as, for example, alkyl groups, aryl groups, or cycloalkyl groups as defined herein, and the like.

Representative examples of an ureido group for use herein include, by way of example, an ureido group having one or more substituents or unsubstituted ureido. The ureido group preferably is an ureido group having 1 to 12 carbon atoms. Examples of the substituents include alkyl groups and aryl groups. Examples of the ureido group include 3-methylureido, 3,3-dimethylureido, and 3-phenylureido.

Representative examples of alkoxy groups for use herein include, by way of example, an alkyl group as defined above attached via oxygen linkage to the rest of the molecule, i.e., of the general formula —OR20, wherein R20 is an alkyl, cycloalkyl, cycloalkylalkyl, cycloalkenyl, aryl or an arylalkyl as defined above, e.g., —OCH3, —OC2H5, or —OC6H5, and the like.

Representative examples of cycloalkyl groups for use herein include, by way of example, a substituted or unsubstituted non-aromatic mono or multicyclic ring system of about 3 to about 18 carbon atoms such as, for example, cyclopropyl, cyclobutyl, cyclopentyl, cyclohexyl, perhydronaphthyl, adamantyl and norbornyl groups bridged cyclic group or spiro-bicyclic groups, e.g., sprio-(4,4)-non-2-yl and the like, optionally containing one or more heteroatoms, e.g., O and N, and the like.

Representative examples of cycloalkylalkyl groups for use herein include, by way of example, a substituted or unsubstituted cyclic ring-containing radical containing from about 3 to about 18 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 18 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 25 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group as defined above directly bonded to an alkyl group as defined above, e.g., —CH2C6H5, —C2H5C6H5 and the like, wherein the aryl group can optionally contain one or more heteroatoms, e.g., O and N, and the like.

Representative examples of fluoroaryl groups for use herein include, by way of example, an aryl group as defined above having one or more fluorine atoms attached to the aryl group.

Representative examples of heterocyclic ring groups for use herein include, by way of example, a substituted or unsubstituted stable 3 to about 15 membered ring radical, containing carbon atoms and from one to five heteroatoms, e.g., nitrogen, phosphorus, oxygen, sulfur and mixtures thereof. Suitable heterocyclic ring radicals for use herein may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, isochromanyl and the like and mixtures thereof.

Representative examples of heteroaryl groups for use herein include, by way of example, a substituted or unsubstituted heterocyclic ring radical as defined above. The heteroaryl ring radical may be attached to the main structure at any heteroatom or carbon atom that results in the creation of a stable structure.

Representative examples of heteroarylalkyl groups for use herein include, by way of example, a substituted or unsubstituted heteroaryl ring radical as defined above directly bonded to an alkyl group as defined above. The heteroarylalkyl radical may be attached to the main structure at any carbon atom from the alkyl group that results in the creation of a stable structure.

Representative examples of heterocyclo groups for use herein include, by way of example, a substituted or unsubstituted heterocylic ring radical as defined above. The heterocyclo ring radical may be attached to the main structure at any heteroatom or carbon atom that results in the creation of a stable structure.

Representative examples of heterocycloalkyl groups for use herein include, by way of example, a substituted or unsubstituted heterocylic ring radical as defined above directly bonded to an alkyl group as defined above. The heterocycloalkyl radical may be attached to the main structure at carbon atom in the alkyl group that results in the creation of a stable structure.

Representative examples of a "polymerizable ethylenically unsaturated organic radicals" include, by way of example, (meth)acrylate-containing radicals, (meth)acrylamide-containing radicals, vinylcarbonate-containing radicals, vinylcarbamate-containing radicals, styrene-containing radicals and the like. In one embodiment, a polymerizable ethylenically unsaturated organic radical can be represented by the general formula:

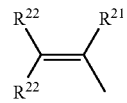

wherein R21 is hydrogen, fluorine or methyl; R22 is independently hydrogen, fluorine, or a —CO—Y—R24 radical wherein Y is —O—, —S— or —NH— and R24 is a divalent alkylene radical having 1 to about 10 carbon atoms.

The substituents in the 'substituted alkyl', 'substituted alkoxy', 'substituted cycloalkyl', 'substituted cycloalkylalkyl', 'substituted cycloalkenyl', 'substituted arylalkyl', 'substituted aryl', 'substituted heterocyclic ring', 'substituted heteroaryl ring,' 'substituted heteroarylalkyl', 'substituted heterocycloalkyl ring', 'substituted cyclic ring' and 'substituted carboxylic acid derivative' may be the same or different and include one or more substituents such as hydrogen, hydroxy, halogen, carboxyl, cyano, nitro, oxo (═O), thio (═S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocycloalkyl ring, substituted or unsubstituted heteroarylalkyl, substituted or unsubstituted heterocyclic ring, substituted or unsubstituted guanidine, —COORx, —C(O)Rx, —C(S)Rx, —C(O)NRxRy, —C(O)ONRxRy, —NRxCONRyRz, —N(Rx)SORy, —N(Rx)SO2Ry, —(═N—N(Rx)Ry), —NRxC(O)ORy, —NRxRy, —NRxC(O)Ry-, —NRxC(S)Ry-NRxC(S)NRyRz, —SONRxRy-, —SO2NRxRy-, —ORx, —ORxC(O)NRyRz, —ORxC(O)ORy-, —OC(O)Rx, —OC(O)NRxRy, —RxNRyC(O)Rz, —RxORy, —RxC(O)ORy, —RxC(O)NRyRz, —RxC(O)Rx, —RxOC(O)Ry, —SRx, —SORx, —SO2Rx, —ONO2, wherein Rx, Ry and Rz in each of the above groups can be the same or different and can be a hydrogen atom, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, 'substituted heterocycloalkyl ring' substituted or unsubstituted heteroarylalkyl, or a substituted or unsubstituted heterocyclic ring.

Preferred monomers of Formula (I) are shown in Formulae (II)-(VI) below:

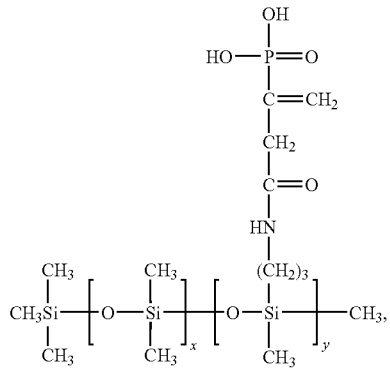
Formula (II)

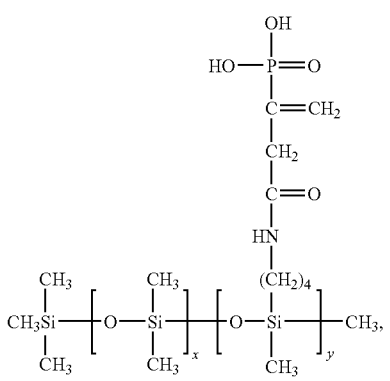
Formula (III)

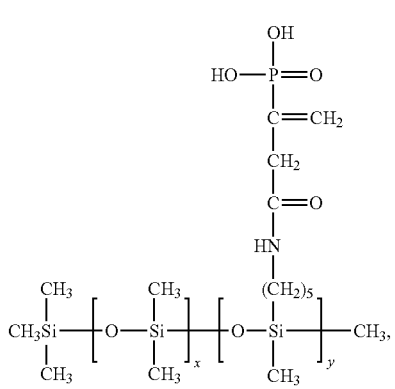
Formula (IV)

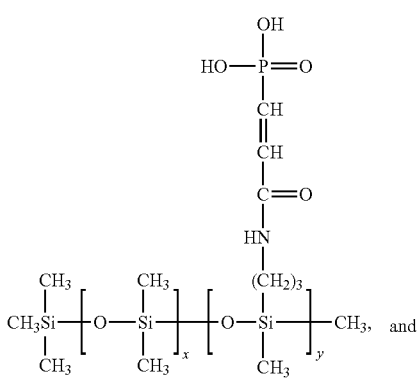
Formula (V)

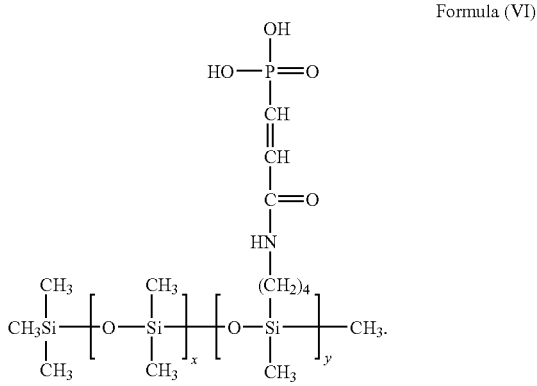
Formula (VI)

A schematic representation of synthetic methods for making the novel hydrophilic siloxy-containing monomers disclosed herein is provided below

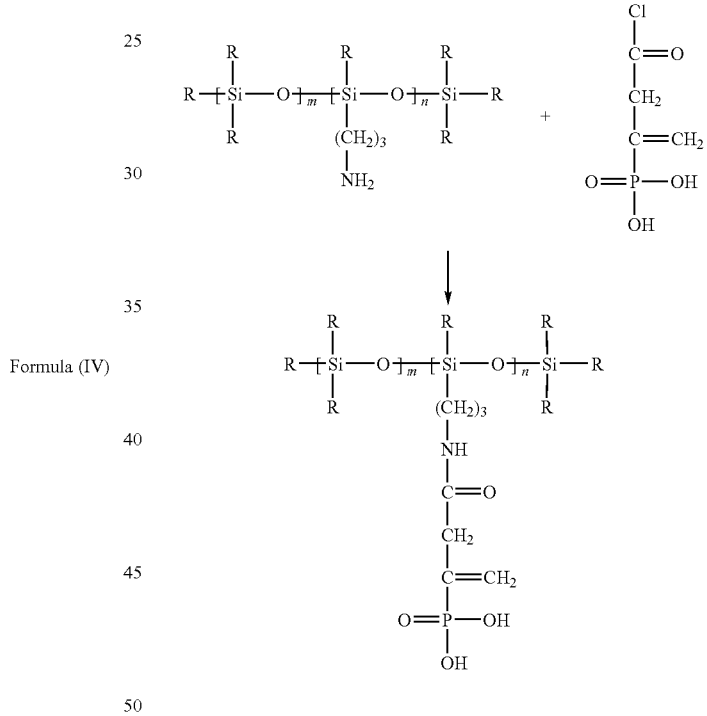

In a second aspect, the invention includes articles formed of device forming monomer mixes comprising the monomers of formula (I). According to preferred embodiments, the article is the polymerization product of a mixture comprising the aforementioned monomer and at least a second monomer. The invention is applicable to a wide variety of polymeric materials, either rigid or soft. Especially preferred polymeric materials are lenses including contact lenses, phakic and aphakic intraocular lenses and corneal implants although all polymeric materials including biomaterials are contemplated as being within the scope of this invention. Preferred articles are optically clear and useful as a contact lens.

The present invention also provides medical devices such as heart valves and films, surgical devices, vessel substitutes, intrauterine devices, membranes, diaphragms, surgical implants, blood vessels, artificial ureters, artificial breast tissue and membranes intended to come into contact with body fluid outside of the body, e.g., membranes for kidney dialysis and heart/lung machines and the like, catheters, mouth guards, denture liners, ophthalmic devices, and especially contact lenses.

Useful articles made with these materials may require hydrophobic, possibly silicon containing monomers. Preferred compositions have both hydrophilic and hydrophobic monomers. Especially preferred is siloxy-containing hydrogels.

Siloxy-containing hydrogels are prepared by polymerizing a mixture containing at least one siloxy-containing monomer and at least one hydrophilic monomer. The siloxy-containing monomer may function as a crosslinking agent (a crosslinker being defined as a monomer having multiple polymerizable functionalities) or a separate crosslinker may be employed.

An early example of a siloxy-containing contact lens material is disclosed in U.S. Pat. No. 4,153,641 (Deichert et al assigned to Bausch & Lomb Incorporated). Lenses are made from poly(organosiloxane) monomers which are $\alpha,\omega$-terminally bonded through a divalent hydrocarbon group to a polymerized activated unsaturated group. Various hydrophobic siloxy-containing prepolymers such as 1,3-bis(methacryloxyalkyl)polysiloxanes are copolymerized with known hydrophilic monomers such as 2-hydroxyethyl methacrylate (HEMA).

U.S. Pat. No. 5,358,995 (Lai et al.) describes a silicon containing hydrogel which is comprised of an acrylic ester-capped polysiloxane prepolymer, polymerized with a bulky polysiloxanylalkyl(meth)acrylate monomer, and at least one hydrophilic monomer. Lai et al. is assigned to Bausch & Lomb Incorporated and the entire disclosure is incorporated herein by reference. The acrylic ester-capped polysiloxane prepolymer, commonly known as $M_2D_x$ consists of two acrylic ester end groups and "x" number of repeating dimethylsiloxane units. The preferred bulky polysiloxanylalkyl (meth)acrylate monomers are TRIS-type (methacryloxypropyltris(trimethylsiloxy)silane) with the hydrophilic monomers being either acrylic- or vinyl-containing.

Other examples of siloxy-containing monomer mixtures which may be used with this invention include the following: vinyl carbonate and vinyl carbamate monomer mixtures as disclosed in U.S. Pat. Nos. 5,070,215 and 5,610,252 (Bambury et al); fluorosilicon monomer mixtures as disclosed in U.S. Pat. Nos. 5,321,108; 5,387,662 and 5,539,016 (Kunzler et al.); fumarate monomer mixtures as disclosed in U.S. Pat. Nos. 5,374,662; 5,420,324 and 5,496,871 (Lai et al.) and urethane monomer mixtures as disclosed in U.S. Pat. Nos. 5,451,651; 5,648,515; 5,639,908 and 5,594,085(Lai et al.), all of which are commonly assigned to assignee herein Bausch & Lomb Incorporated, and the entire disclosures of which are incorporated herein by reference.

Examples of non-silicon hydrophobic materials include alkyl acrylates and methacrylates.

The hydrophilic siloxy-containing monomers disclosed herein may be copolymerized with a wide variety of hydrophilic monomers to produce silicon hydrogel lenses. Suitable hydrophilic monomers include: unsaturated carboxylic acids, such as methacrylic and acrylic acids; acrylic substituted alcohols, such as 2-hydroxyethyl methacrylate and 2-hydroxyethyl acrylate; vinyl lactams, such as N-vinylpyrrolidone (NVP) and 1-vinylazonan-2-one; and acrylamides, such as methacrylamide and N,N-dimethylacrylamide (DMA).

Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art.

Hydrophobic crosslinkers would include methacrylates such as ethylene glycol dimethacrylate (EGDMA) and allyl methacrylate (AMA). In contrast to traditional silicon hydrogel monomer mixtures, the monomer mixtures containing the carboxyl(ate) siloxy-containing monomer of the invention herein are relatively water soluble. This feature provides advantages over traditional silicon hydrogel monomer mixtures in that there is less risk of incompatibility phase separation resulting in hazy lenses, the polymerized materials are extractable with water. However, when desired, traditional organic extraction methods may also be used. In addition, the extracted lenses demonstrate a good combination of oxygen permeability (Dk) and low modulus, properties known to be important to obtaining desirable contact lenses. Moreover, lenses prepared with the carboxyl(ate) siloxy-containing monomers of the invention herein are wettable even without surface treatment, provide dry mold release, do not require solvents in the monomer mix (although solvents such as glycerol may be used), the extracted polymerized material is not cytotoxic and the surface is lubricious to the touch. In cases where the polymerized monomer mix containing the carboxyl(ate) siloxy-containing monomers of the invention herein do not demonstrate a desirable tear strength, toughening agents such as TBE (4-t-butyl-2-hydroxycyclohexyl methacrylate) may be added to the monomer mix. Other strengthening agents are well known to those of ordinary skill in the art and may also be used when needed.

Although an advantage of the hydrophilic siloxy-containing monomers disclosed herein is that they are relatively water soluble and also soluble in their comonomers, an organic diluent may be included in the initial monomeric mixture. As used herein, the term "organic diluent" encompasses organic compounds which minimize incompatibility of the components in the initial monomeric mixture and are substantially nonreactive with the components in the initial mixture. Additionally, the organic diluent serves to minimize phase separation of polymerized products produced by polymerization of the monomeric mixture. Also, the organic diluent will generally be relatively non-inflammable.

Contemplated organic diluents include tert-butanol (TBA); diols, such as ethylene glycol and polyols, such as glycerol. Preferably, the organic diluent is sufficiently soluble in the extraction solvent to facilitate its removal from a cured article during the extraction step. Other suitable organic diluents would be apparent to a person of ordinary skill in the art.

The organic diluent is included in an amount effective to provide the desired effect. Generally, the diluent is included at 5 to 60% by weight of the monomeric mixture, with 10 to 50% by weight being especially preferred.

According to the present process, the monomeric mixture, comprising at least one hydrophilic monomer, at least one hydrophilic siloxy-containing monomer of the invention herein and optionally the organic diluent, is shaped and cured by conventional methods such as static casting or spincasting.

Lens formation can be by free radical polymerization such as azobisisobutyronitrile (AIBN) and peroxide catalysts using initiators and under conditions such as those set forth in U.S. Pat. No. 3,808,179, incorporated herein by reference. Photoinitiation of polymerization of the monomer mixture as is well known in the art may also be used in the process of forming an article as disclosed herein. Colorants and the like may be added prior to monomer polymerization.

Subsequently, a sufficient amount of unreacted monomer and, when present, organic diluent is removed from the cured article to improve the biocompatibility of the article. Release of non-polymerized monomers into the eye upon installation of a lens can cause irritation and other problems. Unlike other monomer mixtures that must be extracted with flammable solvents such as isopropyl alcohol, because of the properties of the novel hydrophilic siloxane monomers disclosed herein, non-flammable solvents including water may be used for the extraction process.

Once the biomaterials formed from the polymerized monomer mix containing the hydrophilic silicon containing monomers disclosed herein are formed they are then extracted to prepare them for packaging and eventual use. Extraction is accomplished by exposing the polymerized materials to various solvents such as water, tert-butanol, etc. for varying periods of time. For example, one extraction process is to immerse the polymerized materials in water for about three minutes, remove the water and then immerse the polymerized materials in another aliquot of water for about three minutes, remove that aliquot of water and then autoclave the polymerized material in water or buffer solution.

Following extraction of unreacted monomers and any organic diluent, the shaped article, for example an RGP lens, is optionally machined by various processes known in the art. The machining step includes lathe cutting a lens surface, lathe cutting a lens edge, buffing a lens edge or polishing a lens edge or surface. The present process is particularly advantageous for processes wherein a lens surface is lathe cut, since machining of a lens surface is especially difficult when the surface is tacky or rubbery.

Generally, such machining processes are performed before the article is released from a mold part. After the machining operation, the lens can be released from the mold part and hydrated. Alternately, the article can be machined after removal from the mold part and then hydrated.

EXAMPLES

All solvents and reagents are obtained from Sigma-Aldrich, Milwaukee, Wis., and used as is. The monomers 2-hydroxyethyl methacrylate and 1-vinyl-2-pyrrolidone are purified using standard techniques.

Analytical Measurements

ESI-TOF MS: The electrospray (ESI) time of flight (TOF) MS analysis is performed on an Applied Biosystems Mariner instrument. The instrument operated in positive ion mode. The instrument is mass calibrated with a standard solution containing lysine, angiotensinogen, bradykinin (fragment 1-5) and des-Pro bradykinin. This mixture provides a seven-point calibration from 147 to 921 m/z. The applied voltage parameters are optimized from signal obtained from the same standard solution. For exact mass measurements poly(ethylene glycol) (PEG), having a nominal $M_n$ value of 400 Da, is added to the sample of interest and used as an internal mass standard. Two PEG oligomers that bracket the sample mass of interest are used to calibrate the mass scale. Samples are prepared as 30 µM solutions in isopropanol (IPA) with the addition of 2% by volume saturated NaCl in IPA. Samples are directly infused into the ESI-TOF MS instrument at a rate of 35 µL/min. A sufficient resolving power (6000 RP m/Δm FWHM) is achieved in the analysis to obtain the monoistopic mass for each sample. In each analysis the experimental monoisotopic mass is compared to the theoretical monoisotopic mass as determined from the respective elemental compositions. In each analysis the monoisotopic mass comparison is less than 10 ppm error. It should be noted that uncharged samples have a sodium (Na) atom included in their elemental composition. This Na atom occurs as a necessary charge agent added in the sample preparation procedure. Some samples do not require an added charge agent since they contain a charge from the quaternary nitrogen inherent to their respective structure.

GC: Gas chromatography is performed using a Hewlett Packard HP 6890 Series GC System. Purities are determined by integration of the primary peak and comparison to the normalized chromatograph.

NMR: $^1$H-NMR characterization is carried out using a 400 MHz Varian spectrometer using standard techniques in the art. Samples are dissolved in chloroform-d (99.8 atom % D), unless otherwise noted. Chemical shifts are determined by assigning the residual chloroform peak at 7.25 ppm. Peak areas and proton ratios are determined by integration of baseline separated peaks. Splitting patterns (s=singlet, d=doublet, t=triplet, q=quartet, m=multiplet, br=broad) and coupling constants (J/Hz) are reported when present and clearly distinguishable.

Mechanical properties and Oxygen Permeability. Modulus and elongation tests are conducted according to ASTM D-1708a, employing an Instron (Model 4502) instrument where the hydrogel film sample is immersed in borate buffered saline; an appropriate size of the film sample is gauge length 22 mm and width 4.75 mm, where the sample further has ends forming a dog bone shape to accommodate gripping of the sample with clamps of the Instron instrument, and a thickness of 200+50 microns.

Oxygen permeability (also referred to as Dk) is determined by the following procedure. Other methods and/or instruments may be used as long as the oxygen permeability values obtained therefrom are equivalent to the described method. The oxygen permeability of siloxy-containing hydrogels is measured by the polarographic method (ANSI Z80.20-1998) using an O2 Permeometer Model 201T instrument (Createch, Albany, Calif. USA) having a probe containing a central, circular gold cathode at its end and a silver anode insulated from the cathode. Measurements are taken only on pre-inspected pinhole-free, flat siloxy-containing hydrogel film samples of three different center thicknesses ranging from 150 to 600 microns. Center thickness measurements of the film samples may be measured using a Rehder ET-1 electronic thickness gauge. Generally, the film samples have the shape of a circular disk. Measurements are taken with the film sample and probe immersed in a bath containing circulating phosphate buffered saline (PBS) equilibrated at 35° C.+/−0.2°. Prior to immersing the probe and film sample in the PBS bath, the film sample is placed and centered on the cathode premoistened with the equilibrated PBS, ensuring no air bubbles or excess PBS exists between the cathode and the film sample, and the film sample is then secured to the probe with a mounting cap, with the cathode portion of the probe contacting only the film sample. For siloxy-containing hydrogel films, it is frequently useful to employ a Teflon polymer membrane, e.g., having a circular disk shape, between the probe cathode and the film sample. In such cases, the Teflon membrane is first placed on the pre-moistened cathode, and then the film sample is placed on the Teflon membrane, ensuring no air bubbles or excess PBS exists beneath the Teflon membrane or film sample. Once measurements are collected, only data with correlation coefficient value (R2) of 0.97 or higher should be entered into the calculation of Dk value. At least two Dk measurements per thickness, and meeting R2 value, are obtained. Using known regression analyses, oxygen permeability (Dk) is calculated from the film samples having at least three different thicknesses. Any film samples hydrated with solutions other than PBS are first soaked in purified water and allowed to equilibrate for at least 24 hours, and then soaked in PHB and allowed to equilibrate for at least 12 hours. The instruments are regularly cleaned and regularly calibrated using RGP standards. Upper and lower limits are established by calculating a +/−8.8% of the Repository values established by William J. Benjamin, et al., The Oxygen Permeability of Reference Materials, Optom Vis Sci 7 (12s): 95 (1997), the disclosure of which is incorporated herein in its entirety:

| Material Name | Repository Values | Lower Limit | Upper Limit |
| --- | --- | --- | --- |
| Fluoroperm 30 | 26.2 | 24 | 29 |
| Menicon EX | 62.4 | 56 | 66 |
| Quantum II | 92.9 | 85 | 101 |

| Abbreviations | |
| --- | --- |
| NVP | 1-Vinyl-2-pyrrolidone |
| TRIS | Methacryloxypropyltris(trimethylsiloxy)silane |
| HEMA | 2-Hydroxyethyl methacrylate |
| v-64 | 2,2'-Azobis(2-methylpropionitrile) |
| PG | 1,3-Propanediol |
| EGDMA | Ethylene glycol dimethacrylate |
| SA | 2-[3-(2H-Benzotriazol-2-yl)-4-hydroxyphenyl]ethyl methacrylate |
| IMVT | 1,4-bis[4-(2-methacryloxyethyl)phenylamino]-anthraquinone |

Unless otherwise specifically stated or made clear by its usage, all numbers used in the examples should be considered to be modified by the term "about" and to be weight percent.

Example 1

Synthesis of Phosphonic Siloxanyl Monomer with Pendant Polymerizable Groups

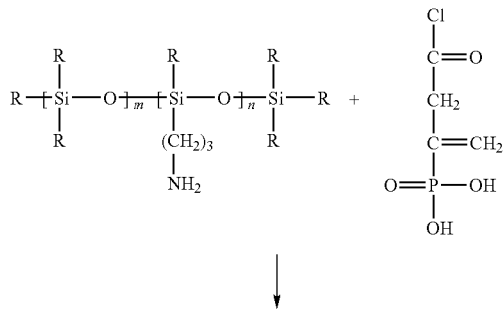

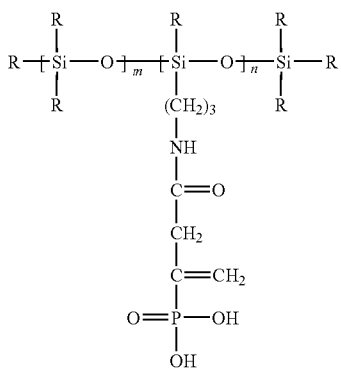

Example 2

Polymerization, processing and properties of films containing phosphonic siloxanyl monomers. Liquid monomer solutions containing carboxylic siloxanyl monomers from example 1 above, along with other additives common to ophthalmic materials (diluent, initiator, etc.) are clamped between silanized glass plates at various thicknesses and polymerized using thermal decomposition of the free-radical generating additive by heating 2 h at 100° C. under a nitrogen atmosphere.

Example 3

Synthesis of phosphonate siloxanyl monomer Using methods well known in the art, the product from example 1 can be converted by treatment with base and optionally ion-exchange to afford phosphonate derivatives as shown below:

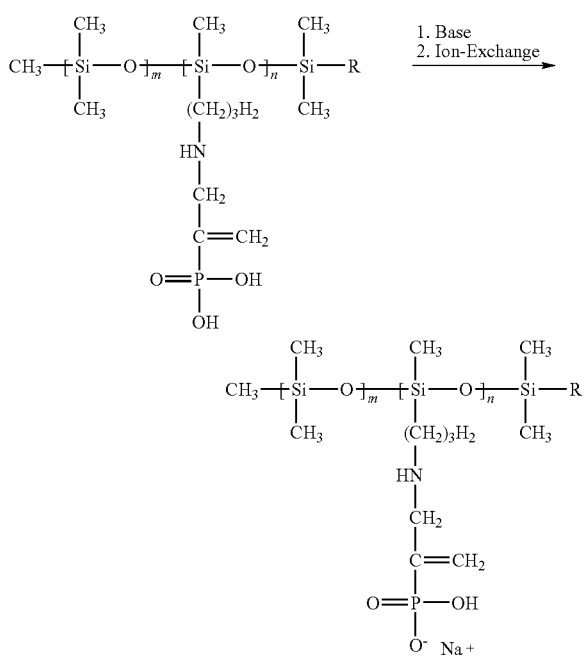

Examples 4-11

Polymerization and processing of films containing phosphonates siloxanyl prepolymers. Liquid monomer solutions containing phosphonate siloxanyl monomer from example 3 above, along with other monomers and additives common to ophthalmic materials (diluent, initiator, etc.) can be clamped between silanized glass plates at various thicknesses and polymerized using thermal decomposition of the free radical generating additive by heating 2 h at 100° C. under a nitrogen atmosphere. Contemplated formulations are listed in table 1.

TABLE 1

| Example | Example 3 | NVP | HEMA | TRIS | HFIPMA | PG | EGDMA | v-64 |
|---|---|---|---|---|---|---|---|---|
| 4 | 10.0 | 0.0 | 10.0 | 50.0 | 25.0 | 4.0 | 0.5 | 0.5 |
| 5 | 10.0 | 20.0 | 0.0 | 45.0 | 20.0 | 4.0 | 0.5 | 0.5 |
| 6 | 25.0 | 25.0 | 10.0 | 0.0 | 35.0 | 4.0 | 0.5 | 0.5 |
| 7 | 10.0 | 50.0 | 10.0 | 25.0 | 0.0 | 4.0 | 0.5 | 0.5 |
| 8 | 10.0 | 25.0 | 10.0 | 25.0 | 25.0 | 0.0 | 0.5 | 0.5 |
| 9 | 10.0 | 25.0 | 10.0 | 25.5 | 25.0 | 4.0 | 0.0 | 0.5 |
| 10 | 35.0 | 50.0 | 10.0 | 0.0 | 0.0 | 4.0 | 0.5 | 0.5 |
| 11 | 45.0 | 50.5 | 0.0 | 0.0 | 0.0 | 4.0 | 0.0 | 0.5 |

Example 12

Films are removed from glass plates and hydrated/extracted in deionized H₂O for a minimum of 4 h, transferred to fresh deionized H₂O and autoclaved 30 min at 121° C. The cooled films are then analyzed for selected properties of interest in ophthalmic materials as described. Mechanical tests are conducted in borate buffered saline according to ASTM D-1708a, discussed above. The oxygen permeabilities, reported in Dk (or barrer) units, are measured in phosphate buffered saline at 35° C., using acceptable films with three different thicknesses, as discussed above.

Example 13

Polymerization and Processing of Ophthalmic Lenses Containing Phosphonate Siloxanyl Prepolymer 40 uL aliquots of a soluble, liquid monomer mix containing 13.9 parts by weight of the product from example 3, 23.3 parts TRIS, 41.8 parts NVP, 13.9 parts HEMA, 5 parts PG, 0.5 parts v-64, 1.5 parts SA, and 60 ppm IMVT are sealed between poly(propylene) anterior and posterior contact lens moulds under an inert nitrogen atmosphere, transferred to an oven and heated under an inert nitrogen atmosphere 2 h at 100° C. The cooled mold pairs are separated and the dry lens released from the mold, hydrated/extracted twice in deionized H2O for a minimum of 3 min, transferred to and sealed in an autoclave vial containing a buffered saline solution and autoclaved 30 min at 121° C.

What is claimed is:

1. A biomedical device comprising a polymerized monomer mixture of a monomer mix comprising
at least one monomer of formula (I)

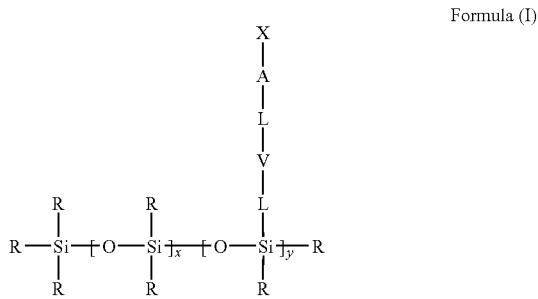

Formula (I)

wherein L can be the same or different and is selected from the group consisting of a bond, a straight or branched C1-C30 alkyl group, a C1-C30 fluoroalkyl group, a C1-C20 ester-containing group, an alkyl ether, cycloalkyl ether cycloalkenyl ether, aryl ether, arylalkyl ether, a polyether containing group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, a C5-C30 fluoroaryl group, or a hydroxyl substituted alkyl ether and combinations thereof; A is a residue capable of forming organic acids, salts or esters selected from the group consisting of sulfonates, sulfates, sulfites, phosphates, phosphites, pyrophosphates and phosphonates; X is H, one equivalent alkali metal, or ½ equivalent alkaline earth metal; R is independently hydrogen, a straight or branched C1-C30 alkyl group, a C1-C30 fluoroalkyl group, a C1-C20 ester-containing group, an alkyl ether, cycloalkyl ether, cycloalkenyl ether, aryl ether, arylalkyl ether, a polyether containing group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, fluorine, a C5-C30 fluoroaryl group, or a hydroxyl group; x and y are each at least 1; and V is independently a polymerizable ethylenically unsaturated organic radical;
and at least one second monomer.

2. The biomedical device of claim 1 wherein the device is a contact lens.

3. The biomedical device of claim 2 wherein the contact lens is a rigid gas permeable contact lens.

4. The biomedical device of claim 2 wherein the contact lens is soft contact lens.

5. The biomedical device of claim 2 wherein the contact lens is a hydrogel contact lens.

6. The biomedical device of claim 1 wherein the device is an intraocular lens.

7. The biomedical device of claim 6 wherein the intraocular lens is a phakic intraocular lens or an aphakic intraocular lens.

8. The biomedical device of claim 1 wherein the device is a corneal implant.

9. A biomedical device comprising a polymerization product of a monomer mixture comprising one or more monomers selected from the group consisting of the following formulae:

Formula (II)
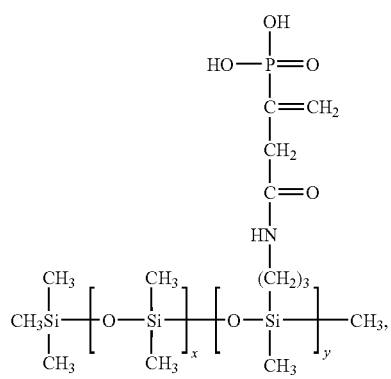

Formula (III)
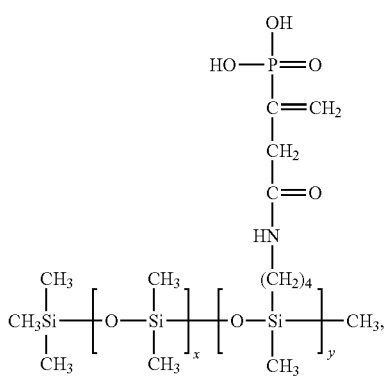

Formula (IV)
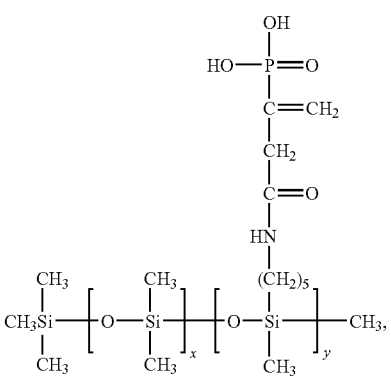

Formula (V)
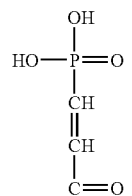
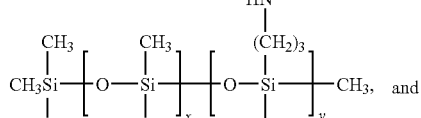, and

Formula (VI)
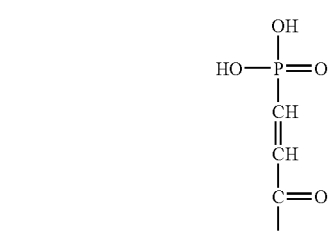

wherein x and y are each at least 1; and a second monomer.

10. The biomedical device of claim 9 wherein the device is a contact lens.

11. A method of making a biomedical device comprising:
providing a monomer mixture comprising the monomer of claim 1 and at least a second monomer;
subjecting the monomer mixture to polymerizing conditions to provide a polymerized device; and
extracting the unpolymerized monomers from the polymerized device.

12. The method of claim 11 wherein the step of extracting is performed with non-flammable solvents.

13. The method of claim 11 wherein the step of extracting is performed with water.

14. The method of claim 11 further comprising the step of packaging and sterilizing the polymerized device.

* * * * *